United States Patent
Evers et al.

(10) Patent No.: US 9,625,542 B2
(45) Date of Patent: Apr. 18, 2017

(54) LOCAL ANTENNA DEVICE FOR TRANSMITTING MAGNETIC RESONANCE SIGNALS

(71) Applicants: Daniel Evers, Otterfing (DE); Klaus Pistor, Neubiberg (DE); Florian Poprawa, Munich (DE); Stefan Schwarzer, Taufkirchen (DE); Markus Vester, Nuremberg (DE)

(72) Inventors: Daniel Evers, Otterfing (DE); Klaus Pistor, Neubiberg (DE); Florian Poprawa, Munich (DE); Stefan Schwarzer, Taufkirchen (DE); Markus Vester, Nuremberg (DE)

(73) Assignee: Siemens Aktiengesellschaft, München (DE)

( * ) Notice: Subject to any disclaimer, the term of this patent is extended or adjusted under 35 U.S.C. 154(b) by 1235 days.

(21) Appl. No.: 13/632,209

(22) Filed: Oct. 1, 2012

(65) Prior Publication Data
US 2013/0082706 A1  Apr. 4, 2013

(30) Foreign Application Priority Data
Sep. 30, 2011  (DE) .......... 10 2011 083 851

(51) Int. Cl.
*G01R 33/34* (2006.01)
*G01R 33/54* (2006.01)
(Continued)

(52) U.S. Cl.
CPC .......... *G01R 33/3692* (2013.01); *A61B 5/055* (2013.01); *G01R 33/34* (2013.01)

(58) Field of Classification Search
CPC ...... G01R 33/34; G01R 33/3692; A61B 5/055
(Continued)

(56) References Cited

U.S. PATENT DOCUMENTS 5,384,536 A    1/1995  Murakami et al.
7,602,187 B2 * 10/2009  Luedeke ................ G01R 33/34
                                                  324/318
(Continued)

FOREIGN PATENT DOCUMENTS

CN   101014870 A   8/2007
CN   200947466 Y   9/2007
(Continued)

OTHER PUBLICATIONS

Chinese Office action for related Chinese Application No. 2012103653072, dated Nov. 26, 2015, with English Translation.
(Continued)

*Primary Examiner* — Melissa Koval
*Assistant Examiner* — Rishi Patel
(74) *Attorney, Agent, or Firm* — Lempia Summerfield Katz LLC

(57) ABSTRACT

A local antenna device for transmitting magnetic resonance (MR) signals of a plurality of MR receiving antenna elements to an MR signal processing device is provided. The local antenna device includes a plurality of analog-to-digital converters for scanning the MR signals and converting the MR signals to digital MR data, and a plurality of transmitting antenna elements for wirelessly transmitting the digital MR data to the MR signal processing device by the emission of an electromagnetic field. The local antenna device includes a plurality of transmitting devices for triggering the transmitting antenna elements and a plurality of spacer elements that is arranged and embodied on the local antenna device such that at least a defined minimum emission spacing is produced between the plurality of transmitting antenna elements and articles adjoining the local antenna device in at least one direction of a principal axis of emission of the electromagnetic field.

20 Claims, 3 Drawing Sheets

(51) Int. Cl.
*G01R 33/36* (2006.01)
*A61B 5/055* (2006.01)

(58) Field of Classification Search
USPC .................. 324/307, 309, 318, 321, 322
See application file for complete search history.

(56) References Cited

U.S. PATENT DOCUMENTS

| | | | |
|---|---|---|---|
| 2007/0108980 A1* | 5/2007 | Adriany | G01R 33/34046 324/318 |
| 2007/0176601 A1 | 8/2007 | Adachi | |
| 2007/0182409 A1 | 8/2007 | Varjo | |
| 2007/0188175 A1* | 8/2007 | Burdick, Jr. | G01R 33/34007 324/322 |
| 2008/0111550 A1* | 5/2008 | Freytag | G01R 33/34007 324/322 |
| 2008/0129298 A1* | 6/2008 | Vaughan | G01R 33/583 324/322 |
| 2008/0272786 A1 | 11/2008 | Luedeke et al. | |
| 2009/0140739 A1 | 6/2009 | Bennett | |
| 2009/0267601 A1 | 10/2009 | Van Helvoort et al. | |
| 2009/0322335 A1 | 12/2009 | Adachi et al. | |
| 2010/0072997 A1 | 3/2010 | Fischer et al. | |
| 2010/0259261 A1 | 10/2010 | Saes et al. | |
| 2010/0308826 A1 | 12/2010 | Saes et al. | |
| 2011/0012598 A1* | 1/2011 | van Helvoort | G01R 33/34 324/318 |
| 2011/0109315 A1* | 5/2011 | Biber | G01R 33/3692 324/318 |

FOREIGN PATENT DOCUMENTS

| | | |
|---|---|---|
| CN | 101052890 A | 10/2007 |
| CN | 101688906 A | 3/2010 |
| CN | 101903791 A | 12/2010 |
| WO | WO03032002 A1 | 4/2003 |
| WO | WO2006008665 A1 | 1/2006 |
| WO | WO2008155703 A1 | 12/2008 |
| WO | WO2009081378 A1 | 7/2009 |

OTHER PUBLICATIONS

Chu, Xu et al. "An Inverse Method to Design RF Coils With Arbitrary Conductor Patterns for MRI Systems," Proceedings of the CSEE, vol. 25, No. 13, 2005.

Chu, Xu et al. "Design of a flat guadrature RF transmit coil for permanent magnet open MRI systems," Magnetic Resonance in Medicine, 2002, vol. 48, No. 1, pp. 203-213.

Chinese office Action for related Chinese Application No. 2012103653072 dated Aug. 15, 2016, with English Translation.

\* cited by examiner

LOCAL ANTENNA DEVICE FOR TRANSMITTING MAGNETIC RESONANCE SIGNALS

This application claims the benefit of DE 10 2011 083 851.1, filed on Sep. 30, 2011.

BACKGROUND

The present embodiments relate to a local antenna device for transmitting magnetic resonance (MR) signals of a number of MR receiving antenna elements to an MR signal processing device.

Imaging systems in medical technology play a significant role in the examination of patients. The images of the patient's internal organs and structures that are generated by the imaging systems are used in the diagnosis of the causes of disease, the planning of operations or the performance of operations or for the preparation of therapeutic measures. Examples of imaging systems of this kind include ultrasound systems, X-ray computed tomography (CT) systems, positron emission tomography (PET) systems, single photon emission tomography (SPECT) systems and MR systems. In the MR systems, during the MR examination, local coils may be used for receiving the MR signals of the examination subject. The local coils are MR receiving antenna modules that contain MR receiving antenna elements (e.g., in the form of conductor loops). During the examination, the local coils are arranged relatively close to the body surface, wherever possible directly on the patient's organ or body part that is to be examined. Unlike relatively large antennas that are arranged further away from the patient, local coils have the advantage that the local coils are arranged closer to the regions of interest. The noise level caused by the electrical losses within the patient's body is reduced, and this has the result that the signal-to-noise ratio (SNR) of a local coil is better than the SNR of an antenna that is further away.

The MR signals that are received by the MR receiving antenna elements may be preamplified while the MR signals are still in the local coil and then fed, by way of cables, out of the central region of the MR system to a shielded receiver of an MR signal processing device. At the shielded receiver of the MR signal processing device, the data received is digitized and processed further for generating images. Where there is a relatively large number of MR receiving antenna elements, there is consequently also a greater need for cables for transmitting the MR signals. However, a large number of cables slows down the attachment of the local coils to the examination subject, resulting in longer treatment times and, hence, higher treatment costs. Many patients find the cables troubling. Further, the examination space is delimited inside an MR system, which limits the use of a large number of cables (e.g., if the patient is moved on an associated table arrangement). The above-mentioned restrictions may be the case if analog MR signals are transmitted by the receiving antenna elements, since shielded (coaxial) cables may be used. The shielded cables are large in cross section, heavy and expensive.

There is, therefore, a need for solutions for transmitting the MR signals to the MR signal processing device that reduce the number of cables needed or avoids the cables completely.

US 2007/0182409 A1 describes an MR system, in which the MR signals are transmitted to a processing device not by way of cables but wirelessly (e.g., by way of optical signals). However, the use of optical signals may require a direct line of sight between the transmitter and the receiver, resulting in corresponding restrictions on the handling of the local coils. WO 2009/081378 A1 provides, for an MR system, a local coil that may both receive and transmit signals wirelessly.

SUMMARY AND DESCRIPTION

The present embodiments may obviate one or more of the drawbacks or limitations in the related art. For example, an improved device and an improved method for transmitting MR signals from MR receiving antenna elements to an MR signal processing device that are rugged, inexpensive and simple to use are provided.

One embodiment of a local antenna device for transmitting MR signals from a number of MR receiving antenna elements to an MR signal processing device includes a number of analog-to-digital converters for scanning the MR signals and converting the MR signals to digital MR data. A "number" may be a positive natural number greater than zero. "Scanning" may be determining the level of the analog MR signal of an MR receiving antenna element at different points in time. In one embodiment, the analog-to-digital converter is arranged in spatial proximity to the MR receiving antenna elements, as a result of which signal losses and signal disruptions are advantageously reduced when analog MR response signals are transmitted. One receiving antenna element or a plurality of receiving antenna elements may be associated with an analog-to-digital converter.

The local antenna device further includes a number of transmitting antenna elements for wirelessly transmitting the digital MR data to the MR signal processing device by way of an electromagnetic field. Various embodiments are may be used. For example, rod antennas, microstrip antennas or dipole antennas may be used. The transmitting antenna elements are adjusted to the frequency, at which the digital MR data is transmitted to the MR signal processing device. A local antenna device may include an individual transmitting antenna element or a plurality of transmitting antenna elements.

The local antenna device includes a number of transmitting devices, by which the transmitting antenna elements are triggered. The transmitting device generates the electrical transmitting power for emitting the electromagnetic field. The transmitting device may provide methods for modulation in order to transmit the MR data to the MR signal processing device by way of the electromagnetic field.

The local antenna device includes a number of spacer elements that are arranged and embodied on the local antenna device such that at least a defined minimum emission spacing is produced or provided between the transmitting antenna elements and articles adjoining the local antenna device in at least one direction of the principal axis of emission of the emitted electromagnetic field. The principal axis of emission describes the axis in the direction, of which the electromagnetic field has the greatest field strength. In the case of symmetrical rod-shaped dipole antennas, for example, a principal axis of emission is produced perpendicular to the principal axes of the rod-shaped antenna elements.

As a result of the spacer elements, the possibility may advantageously be avoided that, when the local antenna device is used in MR imaging, articles abut directly against the transmitting antenna elements or are in the direct vicinity of the transmitting antenna elements. The minimum emission spacing (or minimum spacing) is the spacing that, with the aid of the spacer elements, is maintained at least between an adjoining article and the antenna in the direction of the principal axis of emission. This provides that the spacer elements help the emitted electromagnetic field to propagate to the MR signal processing device with as little disruption as possible from the adjoining articles. During MR imaging, the greatest variety of types of article may adjoin a local coil or a local antenna device (e.g., a patient's clothing, covers, bandaging material, further medical devices and the cabling for these). The spacer elements thus have the effect of reducing or completely avoiding the influence of these articles on the transmission of the digital MR data. Accordingly, the handling of the local antenna device is simplified, since the clinical staff do not have to follow fixed instructions to prevent adjoining or abutment by the articles. This is the case because the spacer elements are a component part of the local antenna device. In other words, the clinical staff do not have to attach any additional devices to the examination subject and remove the additional devices after the imaging. A further advantage is the inexpensive technical implementation of the local antenna device, since the spacer elements are passive components. Consequently, no further active calibration circuits or signals or power supplies therefor are provides for reliable transmission of the MR signals. The properties (e.g., the resonance and reflectance properties) of the transmitting antenna elements and the transmitting devices connected thereto may be optimized as early as during manufacture of the local antenna device, since as a result of the spacer elements, there is a defined environment in the vicinity of the transmitting antenna elements that is not dependent or is dependent only to a small extent on the conditions of use during imaging.

One embodiment of the method for transmitting MR signals of a number of MR receiving antenna elements to an MR signal processing device includes a method act for scanning the MR signals and converting the MR signals to digital MR data, and a further method act for transmitting the digital MR data to a number of transmitting devices. Further, the method includes a method act, in which the digital MR data is transmitted wirelessly to the MR signal processing device by the emission of an electromagnetic field through a number of transmitting antenna elements that are connected to the transmitting devices. A number of spacer elements that are arranged on the local antenna device provide that at least a defined minimum emission spacing is maintained between the transmitting antenna elements and articles adjoining the local antenna device in at least one direction of the principal axis of emission of the electromagnetic field.

In addition to the usual components of a conventional MR system, one embodiment of the MR system includes a local antenna device, as described above. Conventional MR systems may be retrofitted with the equipment by using the local antenna device and, where appropriate, adjusting an existing MR signal processing device. In many cases, adjustment of an MR system in this way will entail only small adjustments to the local coils.

A method for transmitting MR signals or an MR system may be developed in a manner analogous with the local antenna device.

In one embodiment of the local antenna device, the minimum emission spacing corresponds substantially to the size of the near field along the principal axis of emission of the emitted electromagnetic field of the transmitting antenna elements. The near field of an antenna or an antenna element describes the region in the vicinity of the antenna, in which the wave-like propagation of the field may be disrupted to a very great extent by articles that adjoin the antenna or are in the vicinity. The arrangement of the spacer elements thus has the effect that the transmission is not influenced, or is influenced to an acceptable extent, by adjoining articles. The geometric dimensions of the near field around a transmitting antenna element may be described by the wavelength of the emitted electromagnetic field. In the case of simple arrangements of transmitting antenna elements, the field region that is less than twice as far away as the wavelength ($2\lambda$) of the transmitting antenna elements may be designated as the near field. In the case of complex arrangements of the transmitting antenna elements, however, a different minimum emission spacing may be defined in order to achieve the desired reduction in disruptions by adjoining articles. For example, the minimum emission spacing may be greater than twice the wavelength.

For the transmission of the digital MR data to the MR signal processing device, high data rates may be required, since a local antenna device may include a plurality of MR receiving antenna elements that simultaneously receive MR signals during an imaging procedure. Accordingly, the transmission may use frequencies that permit high data rates. The local antenna device may be characterized in that the wavelength of the electromagnetic field is in the millimeter or micron range (e.g., substantially 1.5 cm or substantially 0.5 cm). Thus, it follows from the foregoing that the minimum emission spacing will lie in the range of a few centimeters so that the local coil does not have excessively large dimensions. In one embodiment, the minimum emission spacing is at most 8 cm. In another embodiment, the minimum emission spacing is at least 0.5 cm (e.g., at least 1 cm). Thus, as a function of the above-mentioned wavelength ranges, in one embodiment, the minimum emission spacing may be around 3 cm or more or around 1 cm or more.

In another embodiment of the local antenna, at least one spacer element is embodied as a foil. The foil includes a number of dielectric materials and is in direct contact with the transmitting antenna elements or at a small spacing from the transmitting antenna elements. When a dielectric material is used, the effect that the spacer element has no influence or only a small influence on the emitted electromagnetic field itself may advantageously be produced. A possible influence of the emission of the electromagnetic field may already be taken into account in the embodiment of the local antenna device, since the physical properties of the foil, unlike those of other adjoining articles, are already known. For example, the properties of the foil may be taken into account in the tuning of the transmitting device and the embodiment of the transmitting antenna elements. The use of a foil enables the spacer elements to be shaped in a flexible manner. This is advantageous if local antenna devices are embodied such that the local antenna devices are adapted to specific anatomical conditions (e.g., local antenna devices that serve to generate MR sectional images of a patient's head).

In one embodiment of the local antenna device, the spacer elements are arranged such that an air gap is produced between the spacer elements and the transmitting antenna elements. For example, the spacer elements may be embodied such that the transmitting antenna elements are substantially enclosed by the local antenna device.

In one embodiment, the spacer elements include materials of low relative permittivity, since these materials have only a small influence on the propagation of the electromagnetic field. Materials having a relative permittivity of less than 5 (e.g., materials containing PTFE and/or HDPE (high density polyethylene) and/or epoxy resin (casting resin)) may be used. PTFE may be polytetrafluoroethylene or polytetrafluoroethene, which is also available under various trade names such as, for example, under the trade name Teflon from DuPont. As an alternative or in addition, the spacer elements may include metallic materials (e.g., embodied as metal covers over the transmitting antenna elements).

In one embodiment, the spacer elements are at least partly a component part of the outer delimitation of the local antenna device. As a result of this arrangement, the possibility that the spacer elements will be found troublesome during handling by the clinical staff or the patient is avoided. With an arrangement of this kind, the transmitting property of a local antenna device may be improved without the need to change its usual shape.

In one embodiment, the local antenna device includes a printed circuit board substrate and spacer elements that are connected to the printed circuit board substrate. For example, this is advantageous if the transmitting antenna elements are at least partly enclosed by the printed circuit board substrate because this simplifies the technical implementation of a local antenna device, since standardized, tried-and-tested and inexpensive methods for printed circuit board manufacture may be used. The transmitting antenna elements may be embodied as conductor tracks on the printed circuit board substrate. In this case, the printed circuit board substrate may itself be embodied as or act as a spacer element (e.g., if the transmitting antenna elements are enclosed by the printed circuit board substrate). In other words, the transmitting antenna elements are, for example, formed on wiring levels in the interior of or in cavities in the printed circuit board substrate.

The local antenna device may be embodied such that the local antenna device includes a printed circuit board substrate and the analog-to-digital converters. The transmitting devices and the transmitting antenna elements are arranged on a common printed circuit board substrate. In this case, arrangements, in which the transmitting antenna elements are located on the same side face as the analog-to-digital converters or transmitting devices or are located on opposing side faces, may be provided.

In one embodiment of the local antenna device, the local antenna device includes a number of receiving devices that are connected to the transmitting antenna elements and by which the local antenna device receives MR control signals from the MR signal processing device. The properties of the transmitting device are influenced, by way of the MR control signals, by the MR signal processing device, for example, in order to raise or lower the transmitting power to the transmitting antenna elements.

In one embodiment of the method, the minimum emission spacing is defined such that the near field of the emitted electromagnetic field along the principal axis of emission is not substantially influenced by articles adjoining the local antenna device, and/or the resonant frequency of the transmitting antenna elements is not substantially influenced by articles adjoining the local antenna device. In this case, the foregoing statements on the definition of the near field and the advantageous dimensioning of the minimum emission spacing apply analogously.

BRIEF DESCRIPTION OF THE DRAWINGS

Like components are designated by like reference numerals.

DETAILED DESCRIPTION OF THE DRAWINGS

Figure 1:
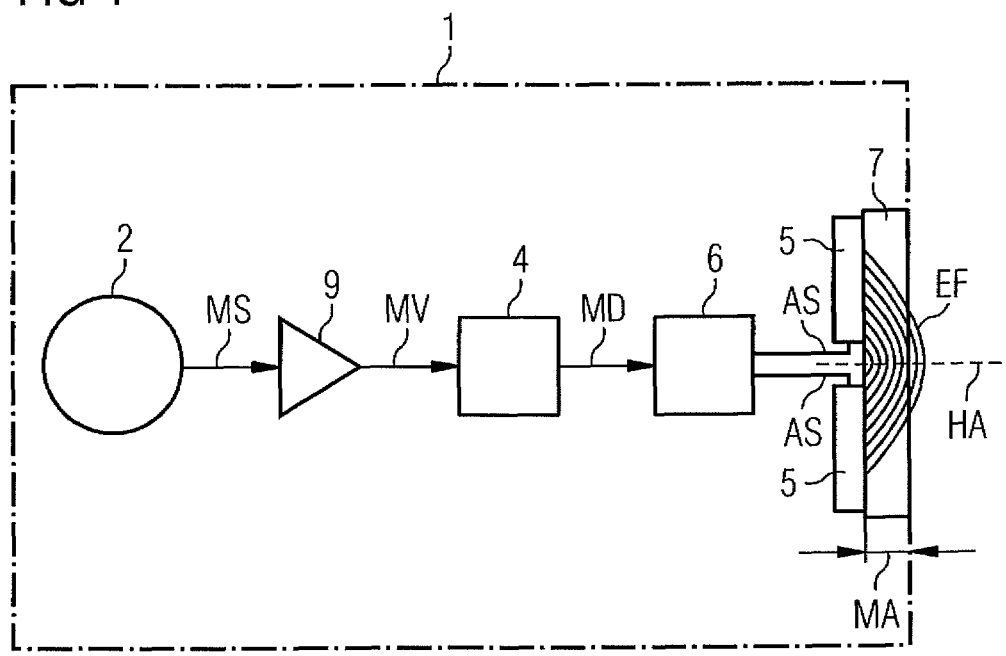
FIG. 1 shows a schematic component layout diagram of one embodiment of a local antenna device.

FIG. 1 shows a schematic component layout diagram of one embodiment of a local antenna device 1. The local antenna device 1 includes a magnetic resonance (MR) receiving antenna element 2, a signal amplifier 9, an analog-to-digital converter 4, a transmitting device 6, two transmitting antenna elements 5 and a spacer element 7.

An MR signal MS that is received by the MR receiving antenna element 2 is passed on to a signal amplifier 9. In addition to linear amplification of the incoming MR signal MS, the signal amplifier 9 may also filter the MR signal MS, for example, in order to reduce or remove portions of thermal noise or signal portions that are caused by other components of an MR system 13. On an output side, the signal amplifier 9 is connected by way of an amplified MR signal MV to the analog-to-digital converter 4.

The analog-to-digital converter 4 scans the amplified MR signals MV and converts the amplified MR signals MV to digital MR data MD. Because the frequency bandwidth of the MR signals MS that are to be transmitted may be dependent on the maximum gradient strength of the magnetic field in the MR system 13 and the size of the patient P or the examination subject, a rate of scanning may be selected as a function of these parameters. The word length and the data rate of the generated digital MR data MD may depend on the scanning rate, the selected conversion method, the available transmission rate and other parameters. For example, the data rate of the digital MR data MD may vary over time during an imaging session. The analog-to-digital converter 4 may, for example, be configured by the delta-sigma method, the flash method, the sawtooth method or another converter method. In addition to conversion, the analog-to-digital converter 4 or a component that is associated with the analog-to-digital converter 4 may bring about a reduction in the data rate and/or word length of the digital MR data MD. On the output side, the analog-to-digital converter 4 is connected to the transmitting device 6.

The transmitting device 6 triggers the transmitting antenna elements 5 by way of antenna signals AS. In addition to generating the transmitting power for the transmitting antenna elements 5, the transmitting device 6 may generate a carrier signal of fixed or time-variable transmission frequency and change the carrier signal as a function of the digital MR data MD, for example, by amplitude modulation or frequency modulation.

In the embodiment shown in FIG. 1, the transmitting antenna elements 5 are embodied as a dipole antenna, but other embodiments such as rod antennas or microstrips may also be used without departing from the scope of the invention. The transmitting antenna elements 5 emit an electromagnetic field EF, by which the digital MR data MD is transmitted wirelessly to an MR signal processing device 3.

Associated with the transmitting antenna elements 5 of the local antenna device 1 is a spacer element 7 that is embodied such that at least a defined minimum emission spacing MA is produced between the transmitting antenna elements 5 and articles adjoining the local antenna device 1 in at least one direction of the principal axis of emission HA of the electromagnetic field EF.

Figure 2:
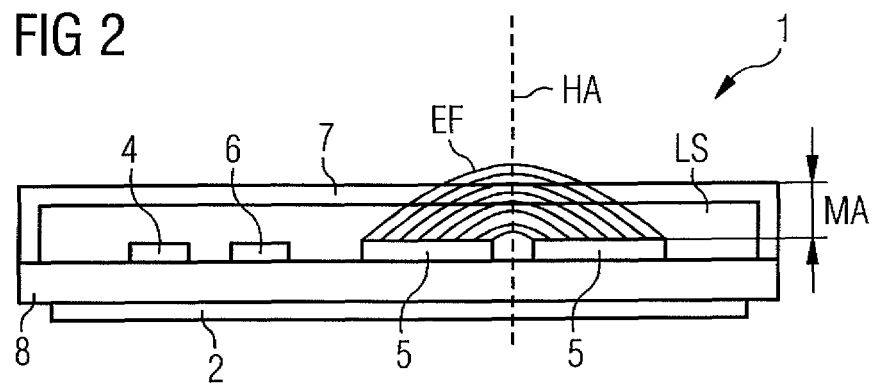
FIG. 2 shows a cross section through one embodiment of a local antenna device.

FIG. 2 represents a cross section through an exemplary embodiment of a local antenna device 1. The local antenna device 1 includes an MR receiving antenna element 2, a signal amplifier 9, an analog-to-digital converter 4, a transmitting device 6, two transmitting antenna elements 5, a spacer element 7 and a printed circuit board substrate 8. For reasons of clarity, the signals and other connections between the individual components of the local antenna device 1 are not shown in FIG. 2.

In this exemplary embodiment, the MR receiving antenna element 2 is arranged on a side face of the printed circuit board substrate 8 (e.g., designated as the underside in FIG. 2) and covered, for example, only by a relatively thin housing wall (not illustrated), while the other components 4, 5, 6 and 7 are arranged on an opposing side face that is designated as the upper side. During MR imaging, the local antenna device 1 may be arranged on the patient P such that the MR receiving antenna elements 2 are located as close as possible to the region of the patient P that is to be examined. The spacer element 7 produces the desired minimum emission spacing MA between the transmitting antenna elements 5 and articles adjoining the local antenna device 1.

In the exemplary embodiment shown in FIG. 2, the spacer element 7 is embodied such that there is an air gap LS between the spacer element 7 and the transmitting antenna elements 5. The spacer element 7 may be embodied in the form of a frame that is connected to the upper side of the printed circuit board substrate 8, or as a cover that, together with the printed circuit board substrate 8, completely encloses the transmitting antenna elements 5. Materials that may be used for a frame or cover of this kind are both metallic materials and also materials having a low relative permittivity, since materials having a low relative permittivity have only a small influence on the propagation of the electromagnetic field EF. In one embodiment, materials having a relative permittivity of less than 5 (e.g., materials containing PTFE and/or HDPE (high density polyethylene)) may be used.

In one embodiment of the local antenna device 1, the MR receiving antenna element 2, the signal amplifier 9, the analog-to-digital converter 4, the transmitting device 6, the transmitting antenna elements 5 and the spacer element 7 are not arranged on a printed circuit board substrate 8 but are spatially separated from one another or are connected to one another partly or completely by way of other components (e.g., frames of synthetic material). The transmitting antenna elements 5 or the spacer element 7 may be embodied in materials that are mechanically flexible.

Figure 3:
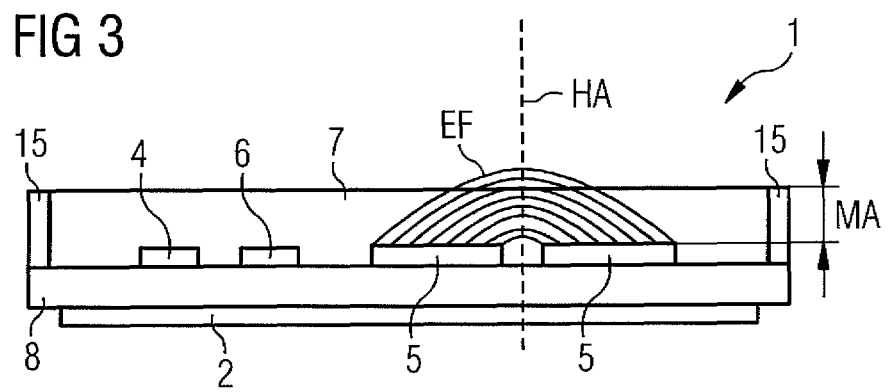
FIG. 3 shows a cross section through another embodiment of a local antenna device.

FIG. 3 shows a cross-section through another exemplary embodiment of a local antenna device 1. The spacer element 7 is embodied by an epoxy or casting resin on an upper side of the printed circuit board substrate 8. The epoxy or casting resin is in direct contact with the transmitting antenna elements 5 and also produces the desired minimum emission spacing MA between the transmitting antenna elements 5 and articles adjoining the local antenna device 1. The spacer element 7 is laterally delimited by a frame 15. In alternative embodiments of the local antenna device 1, only the transmitting antenna elements 5 or only some of the components of the local antenna device 1 may adjoin the epoxy or casting resin.

Figure 4:
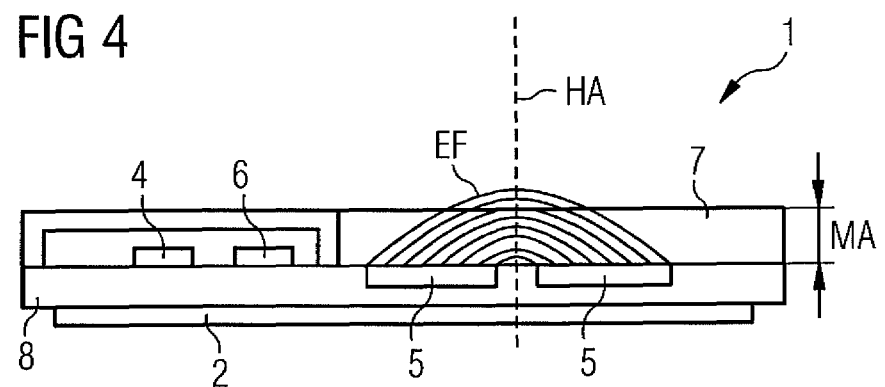
FIG. 4 shows a cross section through yet another embodiment of a local antenna device.

FIG. 4 shows a cross section through an exemplary embodiment of a local antenna device 1. The spacer element 1 is embodied by a foil on the upper side of the printed circuit board substrate 8. The foil is in direct contact with the transmitting antenna elements 5 and also produces the desired minimum emission spacing MA between the transmitting antenna elements 5 and articles adjoining the local antenna device 1. Materials that may be used for a foil of this kind are materials having a low relative permittivity. In one embodiment, materials having a relative permittivity of less than 5 (e.g., materials containing PTFE and/or HDPE (high density polyethylene)) may be used. The transmitting antenna elements 5 are integrated in the printed circuit board substrate 8. For example, the printed circuit board substrate 8 may partly or completely enclose the transmitting antenna elements 5.

Figure 5:
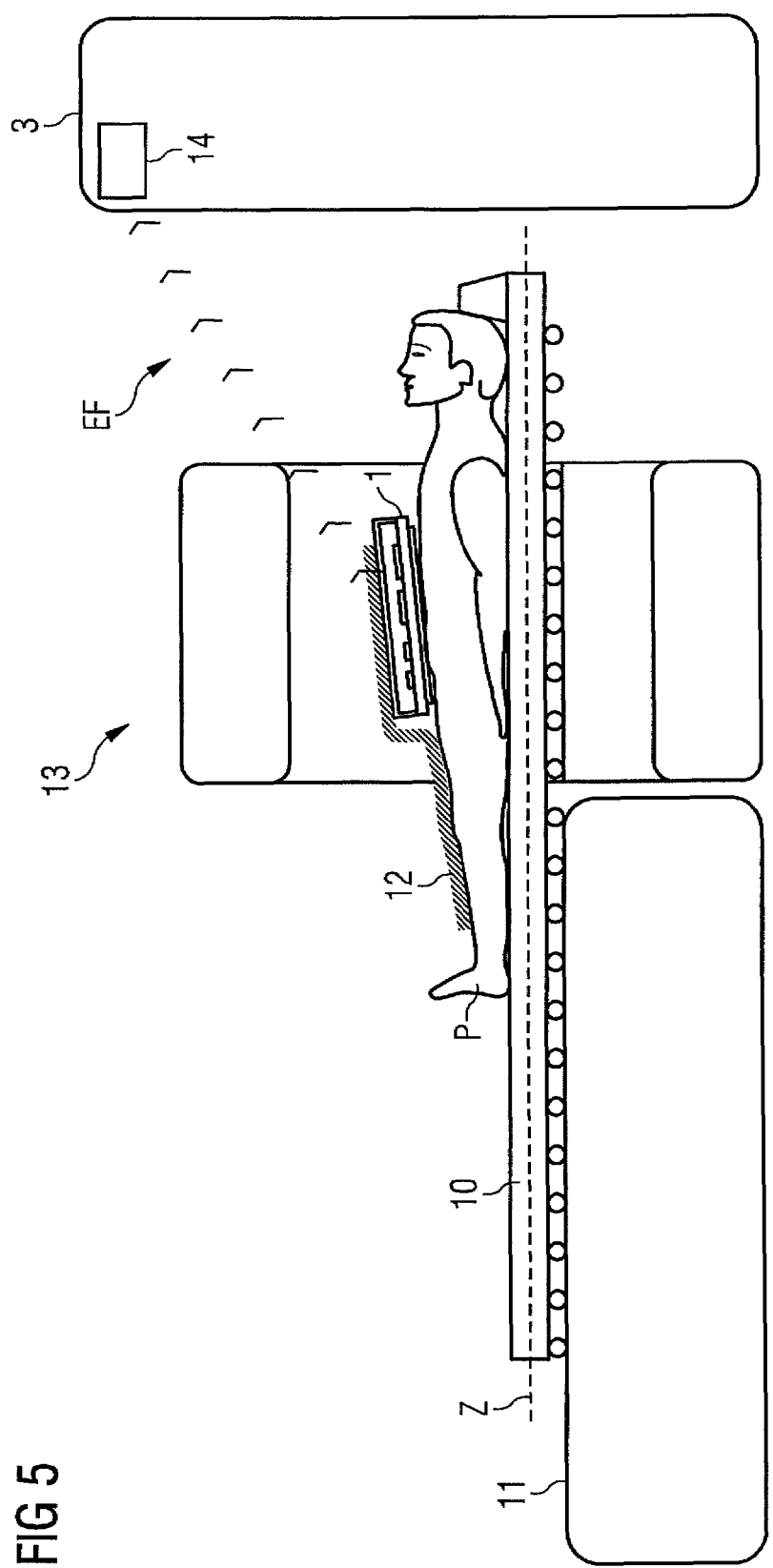
FIG. 5 shows a schematic illustration of a side view of one embodiment of an MR system.

FIG. 5 shows a schematic illustration of a side view of one embodiment of an MR system 13. A patient P lies on a patient table 10 of a table arrangement 11. The patient table 10 may be moved along a longitudinal axis Z to position the patient P for scanning in the interior region of the MR system 13. Arranged on the patient P is a local antenna device 1 according, for example, to the embodiment of FIG. 2. The local antenna device 1 emits an electromagnetic field EF for transmitting the digital MR data MD to the MR signal processing device 3, where the digital MR data MD is received by a receiver 14 and is available for further data processing and imaging.

The patient P and the local antenna device 1 are covered by a patient cover 12. The local antenna device 1 transmits the digital MR data wirelessly by way of an electromagnetic field EF, and the spacer element 7 of the local antenna device 1 provides that there is a minimum emission spacing MA from adjoining articles such as the patient cover 12 that is shown. As a result of these features, advantageously, MR signals MS are reliably transmitted in a typical arrangement in medical MR imaging without the patient P being troubled by cable connections and similar devices. It is not necessary to issue fixed procedural instructions (e.g., instructions on positioning patient covers 12) to the clinical staff to provide reliable transmission.

The local antenna devices and methods described in detail above are merely exemplary embodiments that may be modified by a person skilled in the art in a variety of ways without departing from the scope of the invention. For example, the local antenna device may include a substantially larger number of MR receiving antenna elements than illustrated in FIGS. 1 to 5. For example, an arrangement of a plurality of MR receiving antenna elements in rows and columns, in the form of an antenna array, may be provided. In many cases, the patient will be a person. The use of the term "patient" does not, however, exclude the use of the devices, systems and methods according to the present embodiments in the examination of animals. The use in the examination of healthy persons is also included, for example, for prophylactic reasons or in the examination of volunteers in the context of a clinical study. The use of the indefinite article "a" or "an" does not exclude the possibility that a plurality of the features concerned may also be present. Similarly, the term "unit" or "module" does not exclude the possibility that these include a plurality of components that may, where appropriate, also be spatially distributed. The same also applies to the MR local antenna device, where the components may also be arranged spatially separated from one another in different housings.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A local antenna device for transmitting magnetic resonance (MR) signals of a plurality of MR receiving antenna elements to an MR signal processing device, the local antenna device comprising:
a plurality of analog-to-digital converters operable to scan the MR signals and convert the MR signals to digital MR data;
a plurality of transmitting antenna elements operable to wirelessly transmit the digital MR data to the MR signal processing device by emission of an electromagnetic field;
a plurality of transmitting devices operable to trigger the plurality of transmitting antenna elements;
a substrate that supports the plurality of transmitting antenna elements; and
a plurality of spacer elements arranged on the local antenna device such that at least a defined minimum emission spacing is produced between the plurality of transmitting antenna elements and articles adjoining the local antenna device in at least one direction of a principal axis of emission of the electromagnetic field,
wherein the plurality of transmitting antenna elements are enclosed by the substrate and at least one spacer element of the plurality of spacer elements.

2. The local antenna device as claimed in claim 1, wherein the defined minimum emission spacing corresponds substantially to the size of a near field along the principal axis of emission of the emitted electromagnetic field of the plurality of transmitting antenna elements.

3. The local antenna device as claimed in claim 1, wherein the defined minimum emission spacing is at least 0.5 cm.

4. The local antenna device as claimed in claim 3, wherein the defined minimum emission spacing is at least 1 cm.

5. The local antenna device as claimed in claim 1, wherein at least one spacer element of the plurality of spacer elements comprises a foil, the foil including a plurality of dielectric materials and being in direct contact with the plurality of transmitting antenna elements or at a small spacing from the plurality of transmitting antenna elements.

6. The local antenna device as claimed in claim 1, wherein the plurality of spacer elements is arranged such that an air gap is produced between the plurality of spacer elements and the plurality of transmitting antenna elements.

7. The local antenna device as claimed in claim 1, wherein the plurality of spacer elements includes materials of a relative permittivity.

8. The local antenna device as claimed in claim 7, wherein the plurality of spacer elements includes materials having a relative permittivity of less than 5.

9. The local antenna device as claimed in claim 8, wherein the plurality of spacer elements includes materials including PTFE, HDPE, epoxy resin, or a combination thereof.

10. The local antenna device as claimed in claim 1, wherein the plurality of spacer elements includes metallic materials.

11. The local antenna device as claimed in claim 1, wherein the plurality of spacer elements is at least partly a component part of an outer delimitation of the local antenna device.

12. The local antenna device as claimed in claim 1, wherein the substrate is a printed circuit board substrate, wherein the plurality of spacer elements is connected to the printed circuit board substrate.

13. A magnetic resonance (MR) system for generating MR scans of a region of examination of an examination subject, the MR system comprising:
a plurality of local antenna devices, the plurality of local antenna devices being for transmitting MR signals of a plurality of MR receiving antenna elements to an MR signal processing device, each local antenna device of the plurality of local antenna devices comprising:
a plurality of analog-to-digital converters operable to scan the MR signals and convert the MR signals to digital MR data;
a plurality of transmitting antenna elements operable to wirelessly transmit the digital MR data to the MR signal processing device by emission of an electromagnetic field;
a plurality of transmitting devices operable to trigger the plurality of transmitting antenna elements;
a substrate that supports the plurality of transmitting antenna elements; and
a plurality of spacer elements arranged on the local antenna device such that at least a defined minimum emission spacing is produced between the plurality of transmitting antenna elements and articles adjoining the local antenna device in at least one direction of a principal axis of emission of the electromagnetic field,
wherein the plurality of transmitting antenna elements are enclosed by the substrate and at least one spacer element of the plurality of spacer elements.

14. The MR system as claimed in claim 13, wherein the defined minimum emission spacing corresponds substantially to the size of a near field along the principal axis of emission of the emitted electromagnetic field of the plurality of transmitting antenna elements.

15. The MR system as claimed in claim 13, wherein the defined minimum emission spacing is at least 0.5 cm.

16. The MR system as claimed in claim 13, wherein one or more spacer elements of the plurality of spacer elements comprise a foil, the foil including a plurality of dielectric materials and being in direct contact with the plurality of transmitting antenna elements or at a small spacing from the plurality of transmitting antenna elements.

17. The MR system as claimed in claim 13, wherein the plurality of spacer elements is arranged such that an air gap is produced between the plurality of spacer elements and the plurality of transmitting antenna elements.

18. A method for transmitting magnetic resonance (MR) signals of a number of MR receiving antenna elements of a local antenna device to an MR signal processing device, the method comprising:
scanning the MR signals and converting the MR signals to digital MR data;
transmitting the digital MR data to a plurality of transmitting devices;
wirelessly transmitting the digital MR data to the MR signal processing device by emission of an electromagnetic field through a plurality of transmitting antenna elements connected to the plurality of transmitting devices, a plurality of spacer elements being arranged on the local antenna device, such that at least a defined minimum emission spacing between the plurality of transmitting antenna elements and articles adjoining the local antenna device is provided in at least one direction of a principal axis of emission of the electromagnetic field, wherein the plurality of transmitting antenna elements are completely enclosed by the plurality of spacer elements and a printed circuit board substrate of the local antenna device, the printed circuit board substrate supporting the plurality of transmitting antenna elements.

19. The method as claimed in claim 18, wherein the minimum emission spacing is defined such that a near field of the emitted electromagnetic field along a principal axis of emission is not substantially influenced by the articles adjoining the local antenna device, a resonant frequency of the plurality of transmitting antenna elements is not substantially influenced by the articles adjoining the local antenna device, or a combination thereof.

20. The local antenna device as claimed in claim 1, wherein the plurality of transmitting antenna elements form conductor tracks on the substrate.

* * * * *